(12) United States Patent
Isomura (10) Patent No.: US 9,733,208 B2
(45) Date of Patent: Aug. 15, 2017

(54) GAS SENSOR

(75) Inventor: Hiroshi Isomura, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 433 days.

(21) Appl. No.: 14/131,576

(22) PCT Filed: Aug. 8, 2012

(86) PCT No.: PCT/JP2012/070260
§ 371 (c)(1),
(2), (4) Date: Jan. 8, 2014

(87) PCT Pub. No.: WO2013/024775
PCT Pub. Date: Feb. 21, 2013

(65) Prior Publication Data
US 2014/0144777 A1    May 29, 2014

(30) Foreign Application Priority Data

Aug. 17, 2011 (JP) ................................. 2011-178355

(51) Int. Cl.
| | |
|---|---|
| *G01N 27/407* | (2006.01) |
| *G01N 27/409* | (2006.01) |
| *G01N 27/406* | (2006.01) |

(52) U.S. Cl.
CPC ....... *G01N 27/409* (2013.01); *G01N 27/4067* (2013.01)

(58) Field of Classification Search
CPC ......................................... G01N 27/406–27/41
(Continued)

(56) References Cited

U.S. PATENT DOCUMENTS 4,900,412 A * 2/1990 Ker .................... G01N 27/4067
204/408
5,762,771 A    6/1998 Yamada et al.
(Continued)

FOREIGN PATENT DOCUMENTS

| JP | 60167344 A | 8/1985 |
|---|---|---|
| JP | 62-75461 U | 5/1987 |

(Continued)

OTHER PUBLICATIONS

Notification of Reasons for Rejection dated Jun. 24, 2014, issued by the Japan Patent Office in corresponding application No. 2013-528986.
(Continued)

*Primary Examiner* — Bach Dinh
(74) *Attorney, Agent, or Firm* — Sughrue Mion, PLLC (57) ABSTRACT

A gas sensor according to the present invention includes a sensor element made of a solid electrolyte and having at least a cylindrical portion arranged coaxially with an axis of the sensor element and a front end portion closing a front end of the cylindrical portion and a heater formed into either a cylindrical shape or a cylindrical column shape and located inside the sensor element to heat the sensor element by heat generation thereof, wherein a front end portion of the heater is in contact with an inner surface of the front end portion of the sensor element; and wherein a lateral portion of the heater is in contact with an inner circumferential surface of the cylindrical portion of the sensor element.

10 Claims, 8 Drawing Sheets

(58) Field of Classification Search
USPC .................. 204/424–429; 205/783.5–786
See application file for complete search history.

(56) References Cited

U.S. PATENT DOCUMENTS

| | | | |
|---|---|---|---|
| 5,804,050 A | 9/1998 | Hayakawa et al. | |
| 6,267,857 B1 | 7/2001 | Akatsuka et al. | |
| 6,267,867 B1 | 7/2001 | Olson | |
| 2001/0017057 A1* | 8/2001 | Fukaya | F02D 35/023 73/204.11 |
| 2001/0040092 A1 | 11/2001 | Yanagisawa et al. | |
| 2002/0060152 A1* | 5/2002 | Hotta | G01N 27/4077 204/429 |
| 2003/0217921 A1 | 11/2003 | Dobashi et al. | |
| 2005/0230249 A1* | 10/2005 | Toguchi | G01N 27/407 204/424 |

FOREIGN PATENT DOCUMENTS

| | | |
|---|---|---|
| JP | 4-157358 A | 5/1992 |
| JP | 9-222416 A | 8/1997 |
| JP | 10-54822 A | 2/1998 |
| JP | 144668 A | 2/1999 |
| JP | 1144668 A | 2/1999 |
| JP | 11-247687 A | 9/1999 |
| JP | 2000-35416 A | 2/2000 |
| JP | 2000-46787 A | 2/2000 |
| JP | 2001-74687 A | 3/2001 |
| JP | 2001-133432 A | 5/2001 |
| JP | 2002-5877 A | 1/2002 |
| JP | 2002-31618 A | 1/2002 |
| JP | 2003-344349 A | 12/2003 |
| JP | 2005326396 A | 11/2005 |
| JP | 200778473 A | 3/2007 |

OTHER PUBLICATIONS

Communication dated Jul. 10, 2015, issued by the State Intellectual Property Office of the P.R.C. in corresponding Chinese Application No. 201280039917.1.

* cited by examiner

GAS SENSOR

CROSS REFERENCE TO RELATED APPLICATION

This application is a National Stage of International Application No. PCT/JP2012/070260 filed Aug. 8, 2012, claiming priority based on Japanese Patent Application No. 2011-178355 filed Aug. 17, 2011, the contents of all of which are incorporated herein by reference in their entirety.

FIELD OF THE INVENTION

The present invention relates to a gas sensor suitable for use to detect oxygen etc. in an exhaust gas from an internal combustion engine of a vehicle such as a motorcycle or a passenger car.

BACKGROUND ART

As a gas sensor for detecting the concentration of oxygen in an exhaust gas, there is conventionally known a sensor including an oxygen ion-conducting gas sensing element and mounted for use on an exhaust pipe of an internal combustion engine of a vehicle (see, for example, Patent Documents 1 to 3).

Herein, a general explanation will be given to a gas sensor having the same configuration as those of Patent Documents 1 to 3 (see FIG. 6). In the gas sensor P5, a gas sensing element P1 is fixed in a metal shell P2 with a rear end part of the gas sensing element P1 being covered by a metallic outer tube P3 and by a metallic protection tube P4.

The gas sensing element P1 has an element body (sensor element) made of an oxygen ion-conducting solid electrolyte and at least an inner electrode P7 located inside the element body.

In this type of gas sensor P5, a separator P6 is located rear of the gas sensing element P1 and fixed in position by a rear end portion of the outer tube P3; a metal terminal P8 is placed in contact with the inner electrode P7; and a heater P9 is located inside the gas sensing element P1 and pressed at a front end portion thereof against an inner circumferential surface of the gas sensing element P1 so as to heat the gas sensing element P1.

As mentioned in Patent Documents 1 to 3, the solid electrolyte, which can be formed from a ceramic material such as zirconium oxide, is used as the material of the element body of the gas sensing element P1 (sensor element). In order for the gas sensing element P1 to perform its oxygen sensor function, the gas sensing element P1 needs to be heated to an activation temperature. It is thus common practice to utilize the heater P9 such that the element body of the gas sensing element P1 (sensor element) can be heated to the activation temperature by the heater P9.

There is also a need to raise the temperature of the element body of the gas sensing element P1 (sensor element) to the activation temperature in a short time, that is, a need to allow early activation of the element body of the gas sensing element P1 (sensor element) when the oxygen concentration needs to be detected accurately in a short time e.g. at the time of starting of an internal combustion engine. If the heater P9 is spaced apart from the element body of the gas sensing element P1 (sensor element), it takes time until the heat generated by the heater P9 is conducted to the element body of the gas sensing element P1 (sensor element). This results in a longer time required for activation of the element body of the gas sensing element P1 (sensor element). It is conceivable to bring the heater P9 (more specifically, a heating portion of the heater P9) into direct contact with the element body of the gas sensing element P1 (sensor element) so as to reduce the time required for activation of the element body of the gas sensing element P1 (sensor element).

PRIOR ART DOCUMENTS

Patent Documents

Patent Document 1: Japanese Laid-Open Patent Publication No. 2000-035416
Patent Document 2: Japanese Laid-Open Patent Publication No. 2002-031618
Patent Document 3: Japanese Laid-Open Patent Publication No. 2002-005877

SUMMARY OF THE INVENTION

Problems to be Solved by the Invention

Figure 6:
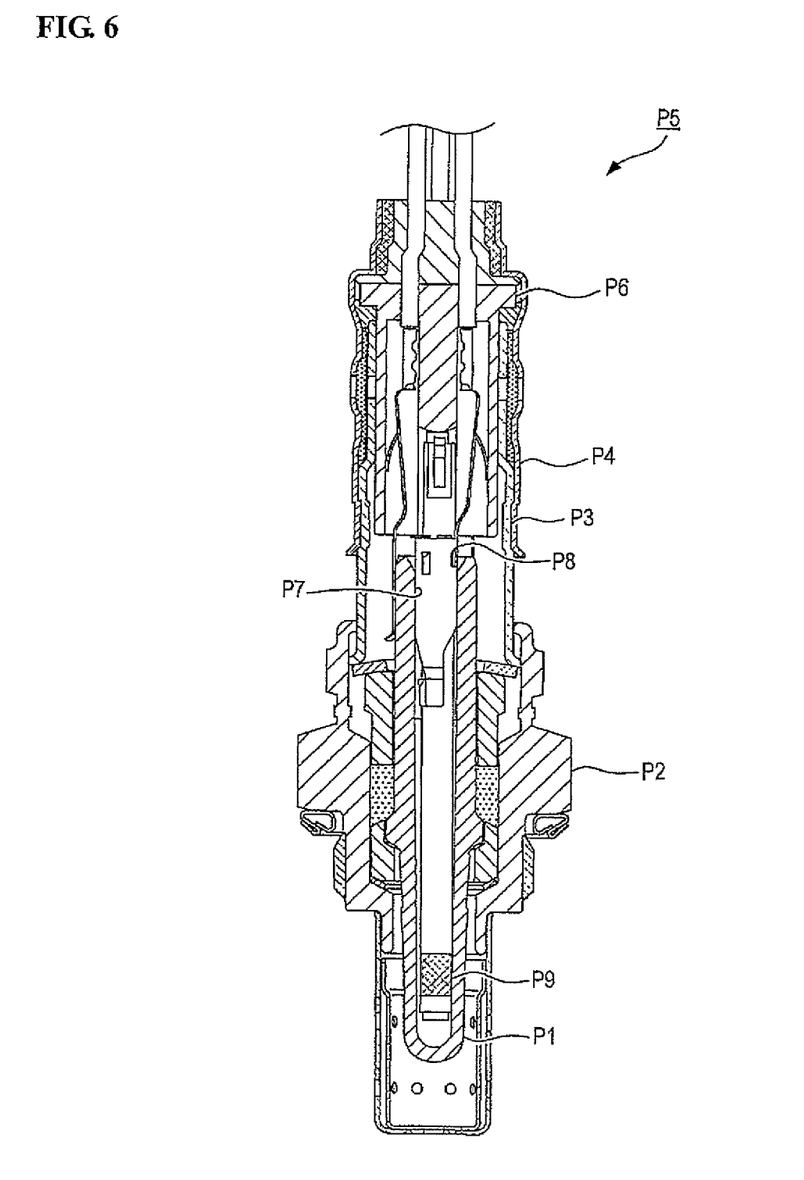
FIG. 6 is a section view showing the overall configuration of a conventional gas sensor.

There are two conceivable ways to bring the heater P9 into direct contact with the element body of the gas sensing element P1 (sensor element) as mentioned above: one way is to bring a lateral surface of the front end portion of the heater P9 into contact with the element body of the gas sensing element P1 (sensor element) as shown in FIG. 6 and the other way is to bring a front end of the heater P9 into contact with the element body of the gas sensing element P1 (sensor element).

In the case where the lateral surface of the heater P9 is brought into contact with the element body of the gas sensing element P1 (sensor element), the heating portion of the heater P9, which reaches the highest temperature, can be placed in direct contact with the element body of the gas sensing element P1 (sensor element), as compared to the case where the front end of the heater P9 is brought into contact with the element body of the gas sensing element P1 (sensor element). It is thus advantageous in that it is easier to conduct the heat to the element body of the gas sensing element P1 (sensor element) and allow early activation of the element body of the gas sensing element P1 (sensor element).

In the case where the front end of the heater P9 is brought into contact with the element body of the gas sensing element P1 (sensor element), by contrast, the heat can be conducted to the inner surface of the front end portion of the element body of the gas sensing element P1 (sensor element) so as to uniformize the temperature distribution in the circumferential direction of the element body of the gas sensing element P1 (sensor element), as compared to the case where the lateral surface of the heater P9 is brought into contact with the element body of the gas sensing element P1 (sensor element). It is thus advantageous in that it is feasible to decrease the temperature difference in the element body of the gas sensing element P1 (sensor element) and limit variations in the output signal from the gas sensing element P1.

In other words, there is a problem that it is difficult to limit variations in the output signal from the element body of the gas sensing element P1 (sensor element) when the lateral surface of the heater P9 is brought into contact with the element body of the gas sensing element P1 (sensor element) with a higher priority given to early activation of the element body of the gas sensing element P1 (sensor element). Further, there is a problem that it takes longer time to activate the element body of the gas sensing element P1 (sensor element) when the front end of the heater P9 is brought into contact with the element body of the gas sensing element P1 (sensor element) with a higher priority given to limiting variations in the output signal from the element body of the gas sensing element P1 (sensor element).

It is therefore one aspect of the present invention to provide a gas sensor capable of not only reducing the time required for activation of an element body of a gas sensing element (sensor element) but also limiting variations in the output from the element body of the gas sensing element (sensor element).

Means for Solving the Problems

The present invention provides the following means.

A gas sensor according to the present invention comprises:

a sensor element made of a solid electrolyte and having at least a cylindrical portion arranged coaxially with an axis of the sensor element and a front end portion closing a front end of the cylindrical portion; and a heater formed into either a cylindrical shape or a columnar shape and located inside the sensor element so as to heat the sensor element by heat generation thereof;

wherein a front end portion of the heater is in contact with an inner surface of the front end portion of the sensor element, and wherein a lateral portion of the heater is in contact with an inner circumferential surface of the cylindrical portion of the sensor element.

In such a configuration, the gas sensor can secure a larger contact area between the heater and the sensor element and enables good heat conduction from the heater to the sensor element as compared to the cases where only the front end portion of the heater is brought into contact with the inner surface of the front end portion of the sensor element and where only the lateral portion of the heater is brought into contact with the inner circumferential surface of the cylindrical portion of the sensor element.

It is therefore possible for the gas sensor according to the present invention to reduce the time required for activation of the sensor element and limit variations in the output from the sensor element.

In this gas sensor, the inner surface of the front end portion of the sensor element may be made flat so as to facilitate bringing the front end and lateral surface of the heater into direct contact with the inner surface of the front end portion and the inner circumferential surface of the cylindrical portion of the sensor element, respectively.

In the case where the inner surface of the front end portion of the sensor element is made flat, it is easier to receive the front end of the heater on the inner surface of the front end portion of the sensor element upon contact thereof and thereby less likely to cause a force that moves the lateral surface of the heater and the inner circumferential surface of the cylindrical portion apart from each other at the time of bringing the front end of the heater into contact with the inner surface of the front end portion of the sensor element while keeping the lateral surface of the heater in contact with the inner circumferential surface of the cylindrical portion of the sensor element. It is thus possible to easily bringing the front end and lateral surface of the heater into direct contact with the inner surface of the front end portion and the inner circumferential surface of the cylindrical portion of the sensor element, respectively. The inner surface of the front end portion of the sensor element may be flat in a direction perpendicular to the axis of the sensor element.

Further, a chamfered portion may be formed on a front end edge of the heater and kept from contact with the inner surface of the front end portion of the sensor element.

As there is clearance left between the chamfered portion on the front end edge of the heater and the inner surface of the front end portion of the sensor element, the chamfered portion on the front end edge of the heater is kept from contact with the inner surface of the front end portion of the sensor element.

The front end edge of the heater can be prevented from interfering with the inner surface of the front end portion of the sensor element. It is thus possible to facilitate bringing the lateral surface of the heater into contact with the inner circumferential surface of the cylindrical portion of the sensor element while bringing the front end of the heater into contact with the inner surface of the front end portion of the sensor element.

The cylindrical portion and the front end portion of the sensor element may be formed integrally with each other so as to define an arc curved surface as a connection region along a boundary between the inner surface of the front end portion and the inner circumferential surface of the cylindrical portion for smooth connection of the inner surface of the front end portion and the inner circumferential surface of the cylindrical portion.

More specifically, the sensor element may satisfy a relationship of $0.3 \leq r/R$ where R is a diameter of the inner circumferential surface of the cylindrical portion of the sensor element; and r is a diameter of the inner surface of the front end portion of the sensor element. The sensor element may further satisfy a relationship of $r/R=0.47$ where R is the diameter of the inner circumferential surface of the cylindrical portion of the sensor element; and r is the diameter of the inner surface of the front end portion of the sensor element.

In the case where the connection region between the inner surface of the front end portion and the inner circumferential surface of the cylindrical portion of the sensor element is formed into such a smooth arc curved shape, it is possible to avoid stress concentration on the connection region and thereby effectively prevent breakage of the sensor element. The range of the arc curved connection region, e.g., the radius of curvature of the connection region may be set so as to keep the front end of the heater, which is in contact with the inner surface of the front end portion, from contact with the connection region, that is, to satisfy the relationship of $0.3 \leq r/R$ or the relationship of $r/R=0.47$. By the formation of such a connection region, it is possible to facilitate bringing the front end and lateral surface of the heater into direct contact with the inner surface of the front end portion and the inner circumferential surface of the cylindrical portion of the sensor element, respectively.

Not only the inner surface of the front end portion of the sensor element but also an outer surface of the front end portion of the sensor element, which defines a front end of the sensor element, may be flat.

In the case where the outer surface of the front end portion of the sensor element, which defines the front end of the sensor element, is made flat, the volume of the front end portion of the sensor element can be made smaller as compared to the case where the outer surface of the front end portion of the sensor element is made spherical in shape. It is thus possible to, even when the sensor element is heated at the same rate, increase the rate of temperature increase of the sensor element in the case where the outer surface of the front end portion of the sensor element is made flat.

Furthermore, a thickness of the front end portion of the sensor element in a direction of the axis may be set larger than or equal to a radial thickness of a region of the cylindrical portion of the sensor element with which the heater is brought into contact.

In the case where the thickness of the front end portion of the sensor element is set larger than or equal to the thickness the cylindrical portion of the sensor element, it is possible to effectively prevent breakage of the sensor element as compared to the case where the thickness of the front end portion of the sensor element is set smaller than the thickness the cylindrical portion of the sensor element. As the front end of the heater collides with the front end portion of the sensor element at the time of insertion of the heater, it is likely that, if the front end portion of the sensor element is insufficient in thickness and poor in strength, a defect such as crack will occur in the front end portion of the sensor element. This defect may develop to a crack under the effect of temperature changes of the sensor element and become a cause of breakage.

The thickness of the front end portion of the sensor element in the direction of the axis may be set equal to the radial thickness of the region of the cylindrical portion of the sensor element with which the heater is brought into contact.

It is possible to decrease the volume of the front end portion of the sensor element while securing the strength of the front end portion of the sensor element in the case where the thickness of the front end portion of the sensor element is set equal to the thickness the cylindrical portion of the sensor element as compared to the case where the thickness of the front end portion of the sensor element is set larger than the thickness the cylindrical portion of the sensor element.

Effects of the Invention

The gas sensor according to the present invention can secure a larger contact area between the heater and the sensor element and enables good heat conduction from the heater to the sensor element as the front end portion and the lateral portion of the heater are brought into contact with the inner surface of the front end portion and the inner circumferential surface of the cylindrical portion of the sensor element, respectively. This makes it easier to conduct the heat from the heater to the solid electrolyte of the element body of the gas sensing element (sensor element) and thereby makes it possible to reduce the time required for activation of the element body of the gas sensing element (sensor element). This also makes it possible to prevent the temperature distribution of the solid electrolyte from becoming nonuniform and limit variations in the output from the element body of the gas sensing element (sensor element).

DESCRIPTION OF REFERENCE NUMERALS

1: Gas sensor
11: Sensor body (Sensor element)
12: Cylindrical portion
13: Front end portion
15: Connection region
16: Outer electrode
19: Inner electrode
20: Heater
25: Chamfered portion

DESCRIPTION OF THE EMBODIMENTS

Figure 1:
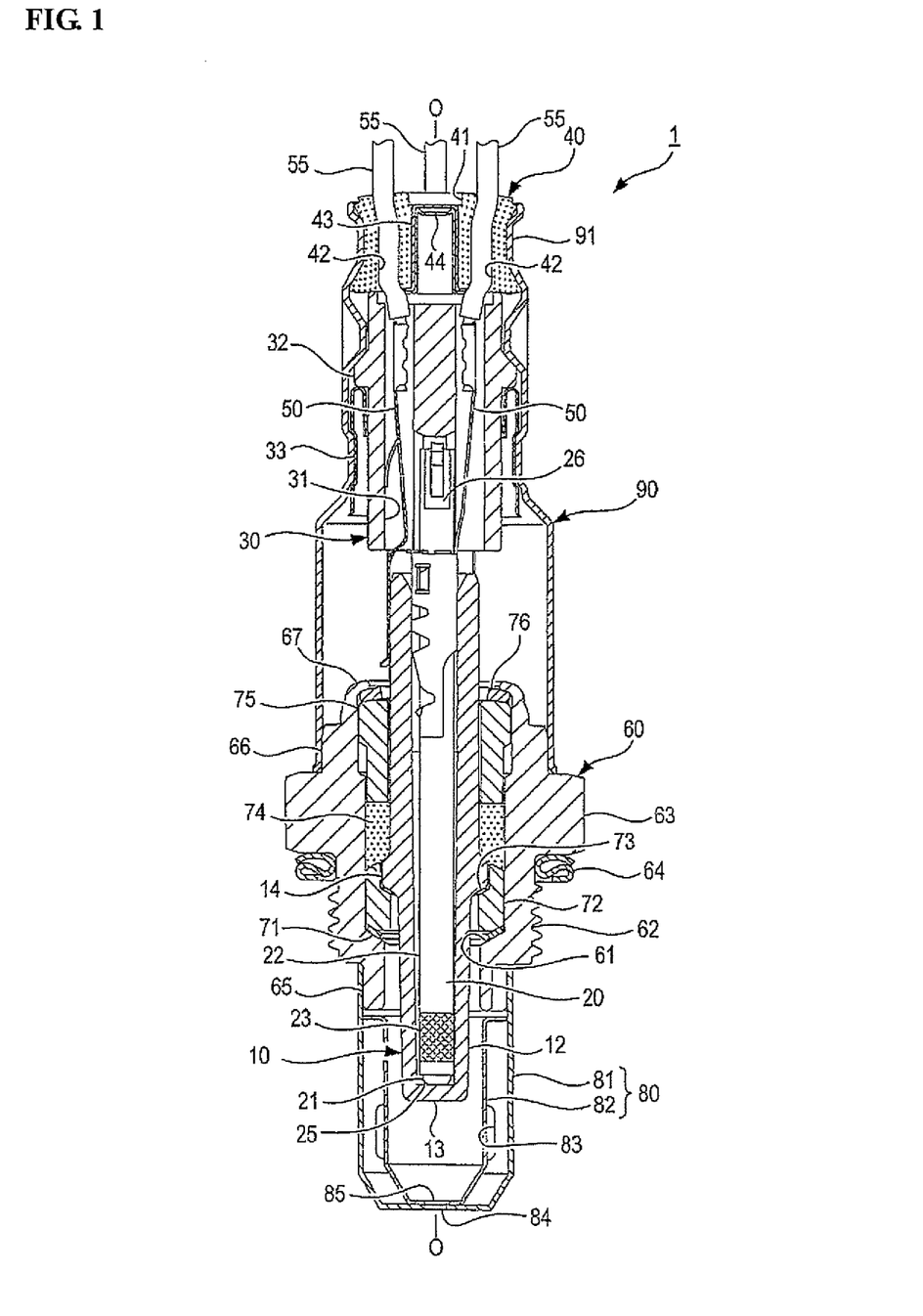
FIG. 1 is a section view showing the overall configuration of a gas sensor according to one embodiment of the present invention.

A gas sensor according to one embodiment of the present invention will be described below with reference to FIGS. 1 to 4. FIG. 1 is a section view of the overall configuration of the gas sensor 1 according to the present embodiment.

In the present embodiment, the gas sensor is embodied as an oxygen gas sensor fixed to a cylinder head of an internal combustion engine of a vehicle such as a passenger car, with a front end part of the gas sensor inserted in an exhaust gas passage inside the cylinder head, so as to measure the concentration of oxygen in an exhaust gas. It is herein noted that, in the following description, the term "front" refers to a side at which a protector 80 is attached to a metal shell 60 with respect to the direction of an axis O; and the term "rear" refers to a side opposite the front side.

The gas sensor 1 according to the present embodiment is of the type having a heater 20 for heating a gas sensing element 10 (discussed later) such that the gas sensing element 10 can be activated by heat of the heater 20 to measure the concentration of oxygen in the exhaust gas.

More specifically, the gas sensor 1 has a gas sensing element 10, a heater 20, a separator 30, a seal member 40, metal terminals 50 and lead wires 55 surrounded by a metal shell 60, a protector 80 and an outer tube 90 as shown in FIG. 1.

Figure 2:
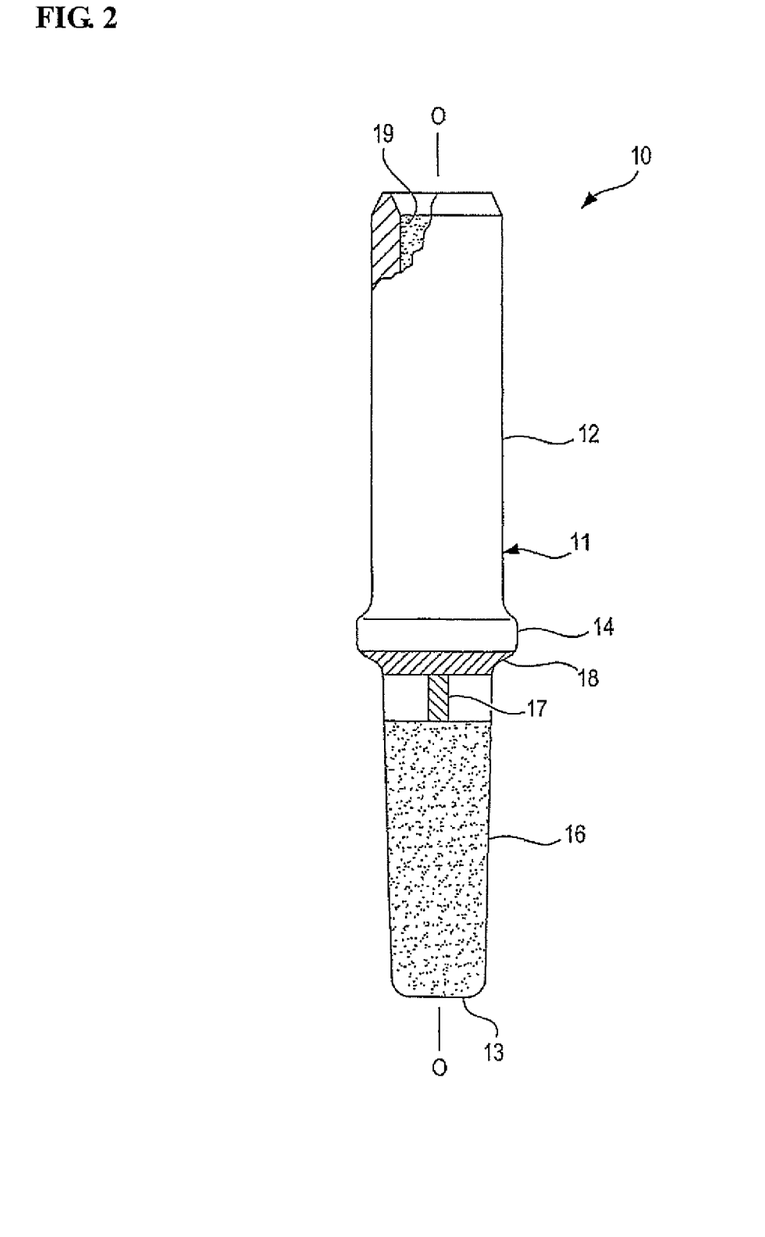
FIG. 2 is a schematic view of a gas sensing element shown in FIG. 1.

FIG. 2 is a schematic view of the gas sensing element 10 of FIG. 1. The gas sensing element 10 includes an element body (sensor element) 11 made of an oxygen ion-conducting solid electrolyte, an outer electrode 16, a vertical lead 17 and an annular lead 18.

The element body 11 (sensor element 11) generally includes a circular cylindrical portion 12 extending in the direction of the axis O and a front end portion 13 closing a front end (lower end in FIG. 2) of the cylindrical portion 12. A radially outwardly protruding flange portion 14 is formed circumferentially around the outer circumference of a center part of the element body 11.

In the present embodiment, the cylindrical portion 12 has an inner circumferential surface formed with a diameter of 3.0 mm. As to the thickness of the element body 11, i.e., the thickness between inner and outer surfaces of the element body 11, a part of the element body 11 directly below the flange portion 14 is 1.0 to 1.5 mm in thickness; and a part of the element body 11 located rear of the flange portion 14 is 2.0 mm in thickness. Further, a front end part of the cylindrical portion 12 is 0.5 mm in thickness. The inner circumferential surface of the cylindrical portion 12 is formed such that at least the vicinity of a front end of the inner circumferential surface, i.e., the vicinity of a region of the inner circumferential surface with which the heater 20 is brought into contact is made constant in diameter.

Figure 3A:
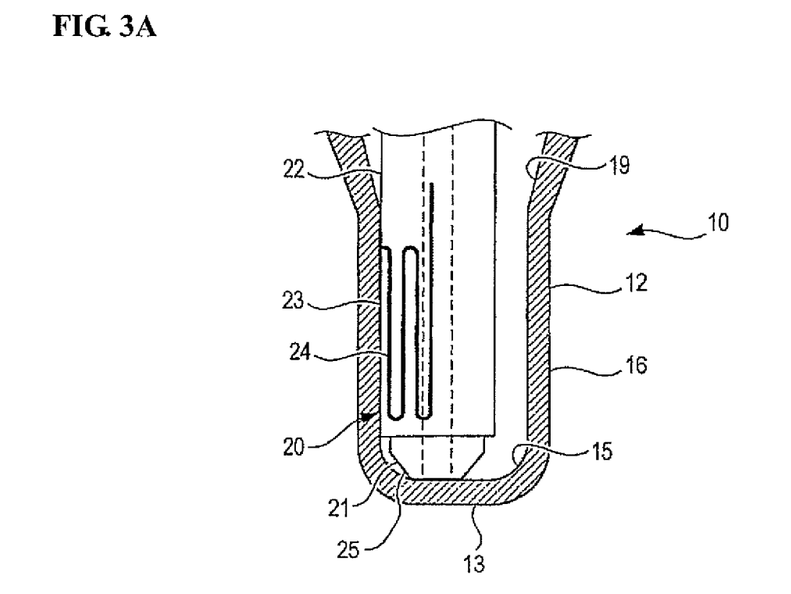
FIGS. 3A and 3B are schematic views of a front end part of the gas sensing element shown in FIG. 1.

As shown in FIGS. 1 and 3A, the front end portion 13 is circular plate-shaped with a thickness of 0.5 mm, which is the same as the thickness of the front end part of the cylindrical portion 12. Namely, both of the inner surface of the front end portion 13 (the surface of the front end portion 13 located inside the element body 11) and the outer surface of the front end portion 13 (the surface of the front end portion 13 located outside the element body 11) are made flat. A connection region 15 is formed as an arc curved surface along a boundary between the inner surface of the front end portion 13 and the inner circumferential surface of the cylindrical portion 12 so that the inner surface of the front end portion 13 and the inner circumferential surface of the cylindrical portion 12 are connected smoothly by the connection region 15.

By the formation of the connection region 15 as such a smooth arc curved surface, it is possible to avoid the occurrence of cracking in the boundary between the inner surface of the front end portion 13 and the inner circumferential surface of the cylindrical portion 12 and thereby effectively prevent breakage of the element body 11.

Figure 3B:
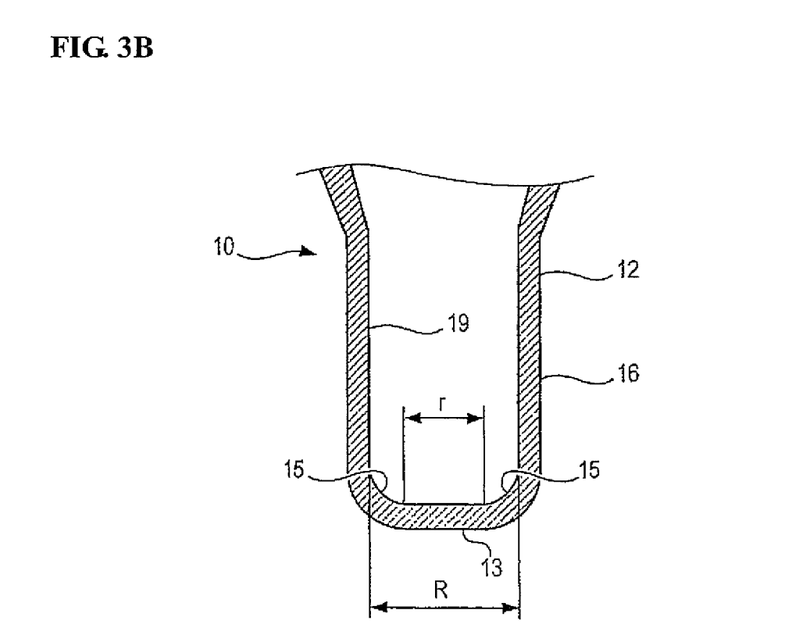

Further, there is satisfied a relationship of $0.3 \leq r/R$ where R is the inner diameter (or inner radius) of the cylindrical portion 12; and r is the diameter (or radius) of the flat region of the inner surface of the front end portion 13 as shown in FIG. 3B. The inner diameter (or inner radius) R of the cylindrical portion 12; and the diameter (or radius) r of the flat region of the inner surface of the front end portion 13 may be set to satisfy a relationship of $r/R=0.47$.

As the solid electrolyte material of the element body 11, a solid solution of $Y_2O_3$ or CaO in $ZrO_2$ is typically usable. It is alternatively feasible to use a solid solution of an oxide of any other alkali earth metal or rare earth metal in $ZrO_2$. Further, $HfO_2$ may be added to the solid solution of alkali earth metal oxide or rare earth metal oxide in $ZrO_2$.

The outer electrode 16, the vertical lead 17 and the annular lead 18 are formed on the outer surface of the element body 11. The outer electrode 16 is made of Pt or Pt alloy (hereinafter referred to as "Pt-based material") in porous form and located on a front end part of the gas sensing element 10. The vertical lead 17 is a conductor made of Pt-based material so as to extend from the outer electrode 16 in the direction of the axis. The annular lead 18 is an annular conductor made of Pt-based material on a lower surface (lower side in FIG. 2) of the flange portion 14 so as to allow electrical conduction with the vertical lead 17. Further, an inner electrode 19 is made of Pt-based material in porous form on the inner circumferential surface of the element body 11.

As shown in FIG. 1, the heater 20 is formed into an elongated shape and located inside the gas sensing element 11 as a heating means for heating the element body 11.

In general, the heater 20 includes a circular ceramic rod 21 made of alumina and a ceramic layer 22 made of alumina and covering an outer circumference of the ceramic rod 21. A heating element 23 is disposed in a front end part of the ceramic layer 22 and adapted to generate heat upon energization thereof. As the heating element 23, a heating resistor 24 is made of any material capable of generating heat upon energization thereof, such as tungsten material, is embedded in the ceramic layer 22 (see FIG. 3A) in the present embodiment. Although the heater is circular rod-shaped in the present embodiment, the shape of the heater is not limited to the circular rod shape. The heater can be formed into a cylindrical shape or columnar shape.

The heater 20 is arranged diagonally relative to the axis of the gas sensing element 10. A front end portion of the ceramic rod 21 of the heater 20 protrudes from the ceramic layer 22 and is brought into direct contact with the flat region of the inner surface of the front end portion 13 of the element body 11. The heating element 23 of the heater 20 is brought into direct contact with the inner lateral circumferential surface of the cylindrical portion 12 of the element body 11. A chamfered portion 25 is formed on a front end edge of the heater 20 and kept from contact with the inner surface (e.g. connection region 15) of the front end portion 13 of the element body 11 (sensor element 11). A pair of electrodes 26 is arranged on a rear end part of the heater 20 and electrically connected to the heating element 23 so as to supply therethrough power to the heating element 23. In FIG. 1, only one of the pair of electrodes 26 is illustrated for the sake of simplicity.

The separator 30 is made of electrically insulating material such as alumina in a cylindrical shape and disposed between the gas sensing element 10 and the seal member 4 as shown in FIG. 1. The separator 30 has an accommodation portion 31 in which the metal terminals 50 and the electrodes 26 are accommodated. The accommodation portion 31 is formed as a through hole passing through the separator 30 in the direction of the axis O so as to allow air communication between the front and rear sides of the separator 30.

A radially outwardly protruding flange portion 32 is formed on an outer circumferential surface of the separator 30. A substantially cylindrical metallic holder member 33 is arranged around the outer circumferential surface of the separator 30 at a position front of the flange portion 32 such that the separator 30 is inserted in the metallic holder member 33.

The seal member 40 is made of elastic material such as fluoro rubber in a cylindrical shape and disposed on a rear end of the gas sensor 1. The seal member 40 is formed as a substantially cylindrical plug having its height direction in agreement with the direction of the axis O to close a rear end of the outer tube 90. The seal member 40 is fitted in the rear open end of the outer tube 90 so as to come into contact with a rear end face of the separator 30 and is fixed in the outer tube 90 by forming an outer tube crimp portion 91 on the outer tube 90 at a position corresponding to a lateral surface of the seal member 40. The outer tube crimp portion 91 is formed into a concave recess shape circumferentially around the outer tube 90 by radially inwardly deforming the outer tube 90. An air communication hole 41 is formed through the radial center of the seal member 40 in the direction of the axis O. Four lead insertion holes 42 are formed through the seal members 40 at circumferentially evenly spaced positions radially outside the air communication hole 41.

The air communication hole 41 is adapted to introduce air to the inside of the outer tube 90, which is closed by the seal member 40. A filter member 43 and a metallic fixing member 44 are inserted in the air communication hole 41. The filter member 43 is a thin-film filter made of e.g. fluoro resin such as PTFE (polytetrafluoroethylene) with a micrometer-scale network structure so as to allow communication of air but not allow permeation of water drops etc. The fixing member 44 is a cylindrical fixture for fixing the filter member 43 in the seal member 40. The filter member 43 is fixed in the seal member 40 by holding the filter member 43 between an outer circumference of the fixing member 44 and an inner circumference of the air communication hole 41.

The four metal terminals 50 are made of nickel alloy (such as Inconel 750; registered trademark of INCO Limited in U.K.) and electrically connected to the outer and inner electrodes 16 and 19 of the element body 11 and the electrodes 26 of the heater 20, respectively. Metal cores of the lead wires 55 are crimped and electrically connected to the respective metal terminals 50. In FIG. 1, three out of four lead wires 55 are illustrated for the sake of simplicity.

The metal shell 60 is made of stainless steel (such as SUS 310S according to JIS) and is substantially cylindrical in shape as shown in FIG. 1. A step portion 61 is formed along the entire circumference of the metal shell 60 so as to protrude radially inwardly from an inner circumferential surface of the metal shell 60 and thereby support thereon the flange portion 14 of the gas sensing element 10.

The metal shell 60 has a thread portion 62 for mounting the gas sensor 1 to cylinder head of the internal combustion engine (not shown) and a hexagonal portion 63 engageable with a mounting tool for screwing the thread portion 62 into the cylinder head. The thread portion 62 and the hexagonal portion 63 are also formed along the entire circumference of the metal shell 60. An annular gasket 64 is arranged between the thread portion 62 and the hexagonal portion 63 so as to prevent gas leakage from the gas sensor 1 and the cylinder head.

A front end fitting portion 65 on which the protector 80 is fitted is formed on the metal shell 60 at a position front of the thread portion 62. An outer circumferential surface of the front end fitting portion 65 is made smaller in diameter than that of the thread portion 62. A rear end fitting portion 66 on which the outer tube 90 is fitted and a crimp fixing portion 67 by which the gas sensing element 10 is fixed by crimping are formed on the metal shell 60 at positions rear of the hexagonal portion 63.

In the metal shell 60, a metallic front packing 71, a cylindrical alumina supporting member 72, a metallic rear packing 53, a filling member 74 of talc powder, an alumina sleeve 75 and an annular ring 76 are placed in order of mention from the step portion 61 toward the rear. A step portion is formed on an inner circumferential surface of the supporting member 72 such that the flange portion 14 of the element body 11 is supported by the step portion. The rear packing 73 is held between the supporting member 72 and the flange portion 14.

The ring 76 is arranged between the sleeve 75 and the crimp fixing portion 67 so as to, when a frontward force is applied by deforming the crimp fixing portion 67 radially inwardly and frontwardly, transmit the applied frontward force to the filling member 74, the rear packing 73, the supporting member 72 and the front packing 71. By this pressing force, the filling member 74 is compressed in the direction of the axis O to hermetically seal the clearance between the inner circumferential surface of the metal shell 60 and the outer circumferential surface of the element body 11.

The protector 80 is adapted to protect the gas sensing element 10, which protrudes inside the gas passage in the state that the gas sensor 1 is fixed to the cylinder head, from collision with water drops and foreign matter etc. flowing through the gas passage. The protector 80 is made of stainless steel (such as SUS 310S according to JIS) and formed as a protection member to cover the front end part of the gas sensing element 10. The protector 80 has a cylindrical shape formed in the direction of the axis with a closed front end. A rear edge portion of the protector member 80 is fixed by welding to the front end fitting portion 65 of the metal shell 60.

In the present embodiment, the protector 80 consists of a bottomed cylindrical outer protector member 81 having an open circumferential edge portion fitted on the front end fitting portion 65 and a bottomed cylindrical inner outer protector member 82 fixed in the outer protector member 81. Namely, the protector 80 has a double structure of the outer and inner protector members 81 and 82.

Introduction holes 83 are formed in circumferential surfaces of the outer and inner protector members 81 and 82 so as to introduce the gas to the sensor inside. In FIG. 1, only the introduction holes 83 of the outer protector member 81 are illustrated; and the introduction hole 83 of the inner protector member 82 are not illustrated for the sake of convenience of arrangement. Further, outer and inner discharge holes 84 and 85 are formed in bottom surfaces of the outer and inner protector members 81 and 82, respectively, so as to discharge the entered water drops and gas to the sensor outside.

The outer tube 90 is made of stainless steel (such as SUS 304L according to JIS) different in kind from that of the metal shell 60 and is fixed to the metal shell 60 by inserting the rear end fitting portion 66 of the metal shell 60 into the outer tube 90. The rear end part of the gas sensing element 10 protruding from the rear end of the metal shell 30 is placed together with the separator 30 and the seal member 40 within the outer tube 90.

In the above configuration, the inner surface of the front end portion 13 of the element body 11 is made flat so that the front end and lateral surface of the heater 20 can be easily respectively brought into direct contact with the inner surface of the front end portion 13 and the inner circumferential surface of the cylindrical portion 12 of the element body 11. It is therefore possible to raise the temperature of the element body 11 in a short time and reduce the time required for activation of the gas sensing element 10 as compared to the cases where only the front end of the heater 20 is brought into the inner surface of the front end portion 13 of the element body 11 and where only the lateral surface of the heater 20 is brought into contact with the inner circumferential surface of the cylindrical portion 12 of the element body 11. It is also possible to uniformize the temperature distribution of the front end of the element body 11 and limit variations in the output of the gas sensing element 10.

For example, it is assumed that the inner surface of the front end portion 13 is spherical in shape. In this case, it is likely that the front end of the heater 20 will be slid on the spherical inner surface of the front end portion 13 and led to the center of the inner surface of the front end portion 13 at the time of bringing the front end of the heater 20 into contact with the inner surface of the front end portion 13 while keeping the lateral surface of the heater 20 in contact with the inner circumferential surface of the cylindrical portion 12. As the lateral surface of the heater 20 and the inner circumferential surface of the cylindrical portion 12 tend to be apart from each other, it becomes difficult to bring the front end and lateral surface of the heater 20 into direct contact with the inner surface of the front end portion 13 and the inner circumferential surface of the cylindrical portion 12, respectively.

In the case where the inner surface of the front end portion 13 is made flat, on the other hand, it is easier to receive the front end of the heater 20 on the inner surface of the front end portion 13 upon contact thereof and thereby less likely to cause a force that moves the lateral surface of the heater 20 and the inner circumferential surface of the cylindrical portion 12 apart from each other at the time of bringing the front end of the heater 20 into contact with the inner surface of the front end portion 13 while keeping the lateral surface of the heater 20 in contact with the inner circumferential surface of the cylindrical portion 12. It is thus possible to facilitate bringing the front end and lateral surface of the heater 20 into direct contact with the inner surface of the front end portion 13 and the inner circumferential surface of the cylindrical portion 12, respectively. The inner surface of the front end portion 13 may be flat in a direction perpendicular to the axis of the element body 11.

In the case where the front end of the element body 11, that is, the outer surface of the front end portion 13 is made flat, the volume of the front end portion 13 can be made smaller than in the case where the outer surface of the front end portion 13 is made spherical in shape. It is thus possible to, even when the element body 11 is heated at the same rate, increase the rate of temperature increase of the element body 11 and reduce the time required for activation of the gas sensing element 10 in the case where the outer surface of the front end portion 13 is made flat.

Furthermore, the thickness of the front end portion 13 is the same as the thickness of the cylindrical portion 12. It is thus possible to decrease the volume of the front end portion 13 while securing the strength of the front end portion 13 as compared to the case where the thickness of the front end portion 12 is made larger than the thickness of the cylindrical portion 12.

In the gas sensor 1, there is a clearance left between the chamfered portion 25 on the front end edge of the heater 20 and the inner surface of the front end portion 13 of the element body 11 (sensor element 11) so that the chamfered portion 25 on the front end edge of the heater 2 is kept from contact with the inner surface of the front end portion 13 of the element body 11 (sensor element 11).

As the front end edge of the heater 2 can be prevented from interfering with the inner surface of the front end portion 13 of the element body 11 (sensor element 11), it is possible to facilitate bringing the lateral surface of the heater 20 into contact with the inner circumferential surface of the cylindrical portion 12 while bringing the front end of the heater 20 in contact with the inner surface of the front end portion 13.

Herein, the correspondence of terminologies between the scope of claims and the above embodiment are as follows. By way of example, the element body 11 (sensor element 11) corresponds to the claimed sensor element; the cylindrical portion 12 corresponds to the claimed cylindrical portion; the front end portion 13 corresponds to the claimed front end portion; the connection region 15 corresponds to the claimed connection region; and the heater 20 corresponds to the claimed heater.

Although the present invention has been described with reference to the above specific embodiments, the present invention is not limited to these specific embodiments. Modification and variation can be made without departing from the scope of the present invention.

Figure 4:
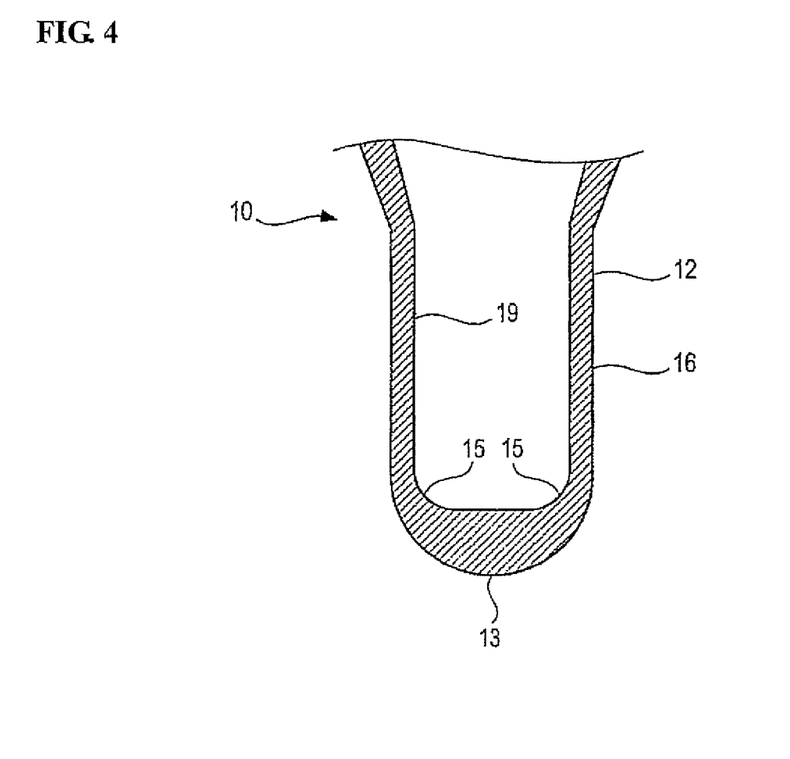
FIG. 4 is a schematic view of a modified example of the front end part of the gas sensing element shown in FIGS. 3A and 3B.

For example, the outer surface of the front end portion 13 of the element body 11 may be made flat as shown in FIGS. 3A and 3B. The outer surface of the front end portion 13 may alternatively be formed into a curved shape such as semispherical curved shape for smooth connection to the outer circumferential surface of the cylindrical portion 12 as shown in FIG. 4. There is no particular limitation on the shape of the outer surface of the front end portion 13 of the element body 11.

In the case where the outer surface of the front end portion 13 is formed into such a curved shape, the thickness of the front end portion 13 of the element body 11 is made larger than the thickness of the cylindrical portion 12 of the element body 11 so that it is possible to effectively prevent breakage of the front end portion 13 as compared to the case where the thickness of the front end portion 13 of the element body 11 is made smaller than the thickness of the cylindrical portion 12 of the element body 11. As the front end of the heater 20 collides with the front end portion 13 of the element body 11 at the time of insertion of the heater 20, it is likely that, if the front end portion 13 is insufficient in thickness and poor in strength, a defect such as crack will occur in the front end portion 13 of the element body 11. This defect may develop to a crack under the effect of temperature changes of the element body 11 and become a cause of breakage.

Figure 5A:
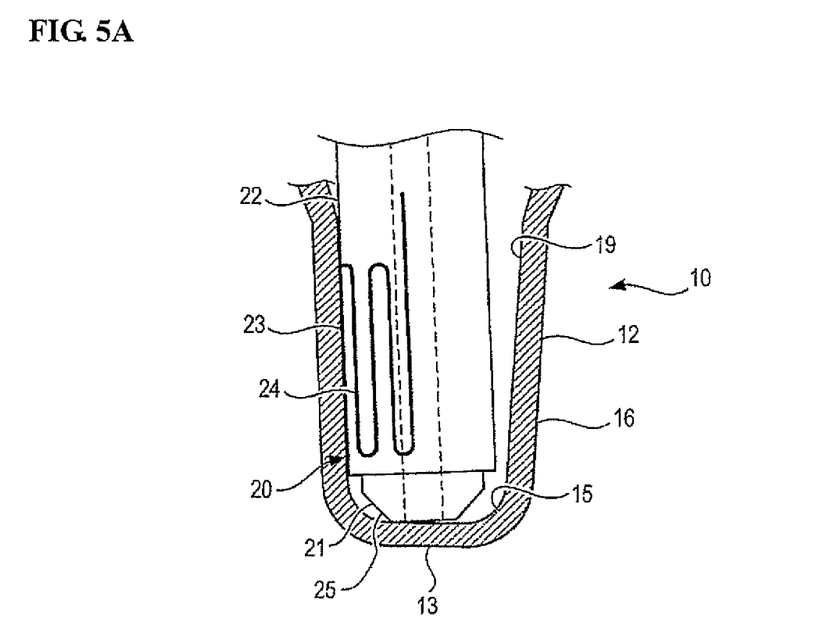
FIGS. 5A and 5B are schematic views of other modified examples of the front end part of the gas sensing element shown in FIGS. 3A and 3B.
Figure 5B:
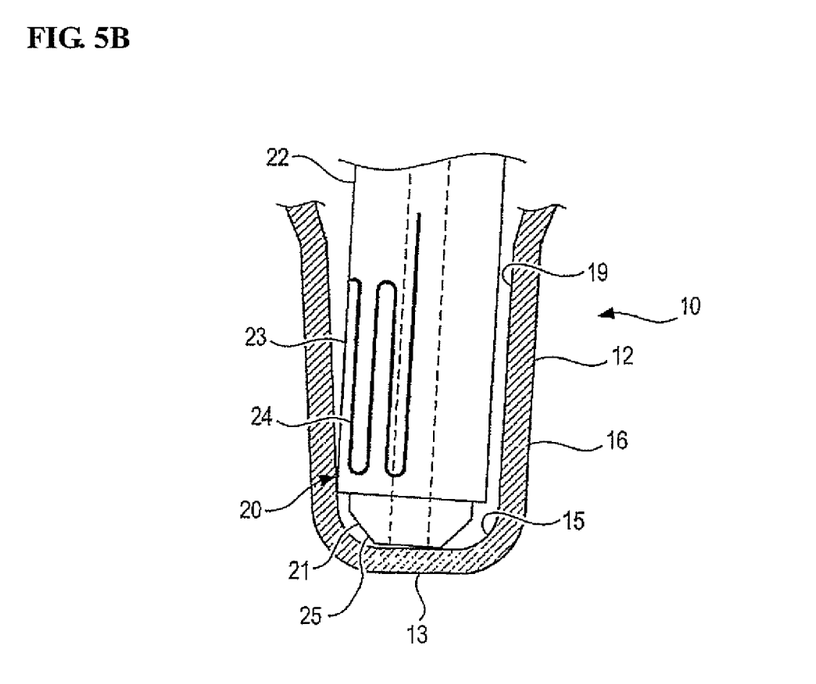

As shown in FIGS. 5A and 5B, the cylindrical portion 12 of the element body 11, including even its front end region with which the heater 20 is brought into contact, may be tapered in such a manner that the inner circumferential diameter of the cylindrical portion 12 decreases in diameter toward the front end portion 13. In this case, it is feasible to incline the heater 20 so as to allow line contact of the ceramic layer 22 of the heater 20, more specifically, the heating element 23 with the inner circumferential surface of the cylindrical portion 12 as shown in FIG. 5A or feasible to incline the heater 20 in an opposite direction to FIG. 5A so as to allow contact of the front end of the ceramic layer 22 with the inner circumferential surface of the cylindrical portion 12 as shown in FIG. 5B. There is no particular limitation on the inclination of the heater 20.

Next, an explanation will be given of results of comparative measurement test of the gas sensor to which the present invention is applied and two comparative (conventional) gas sensors. The comparative measurement test was conducted for three items: "temperature difference between different sensor element regions", "sensor activation time" and "sensor output variations".

One of the comparative (conventional) gas sensors was of the type where a heater is brought into contact with a lateral inner surface of a sensor element (i.e. so called "lateral-contact-structure") as shown in FIG. 6. The other comparative (conventional) gas sensor was of the type where a heater is brought into contact with a front inner end surface of a sensor element (i.e. so called "front-contact-structure").

Figure 7:
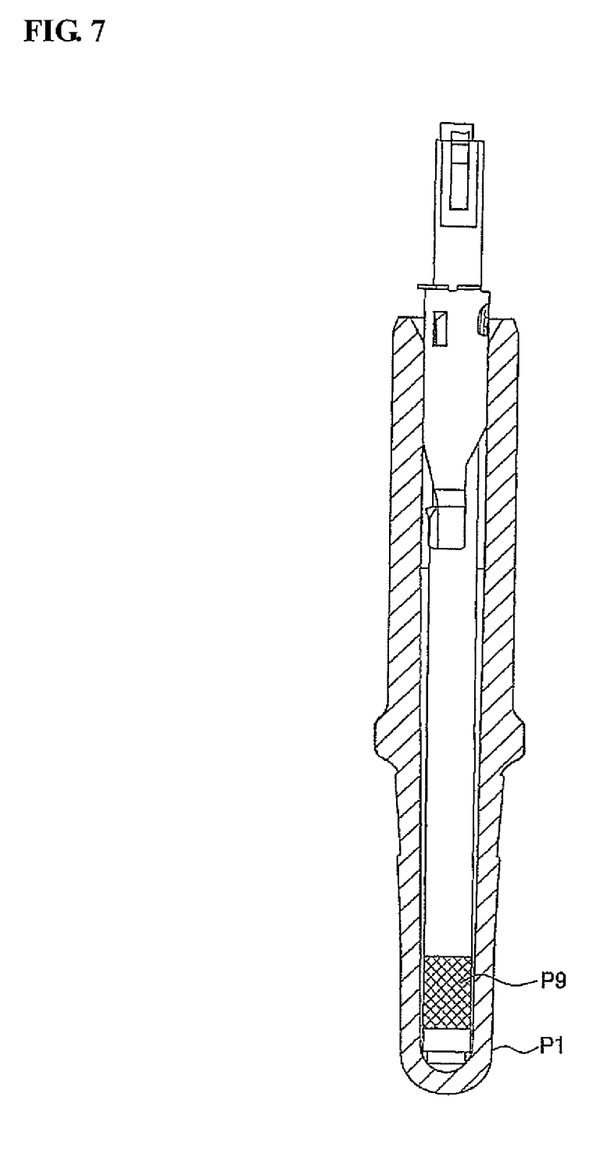
FIG. 7 is a section view of a gas sensing element and a heater in a conventional, front-contact-structure gas sensor.

FIG. 7 is a section view of a gas sensing element P1 and a heater P9 in a front-contact-structure gas sensor.

Figure 8:
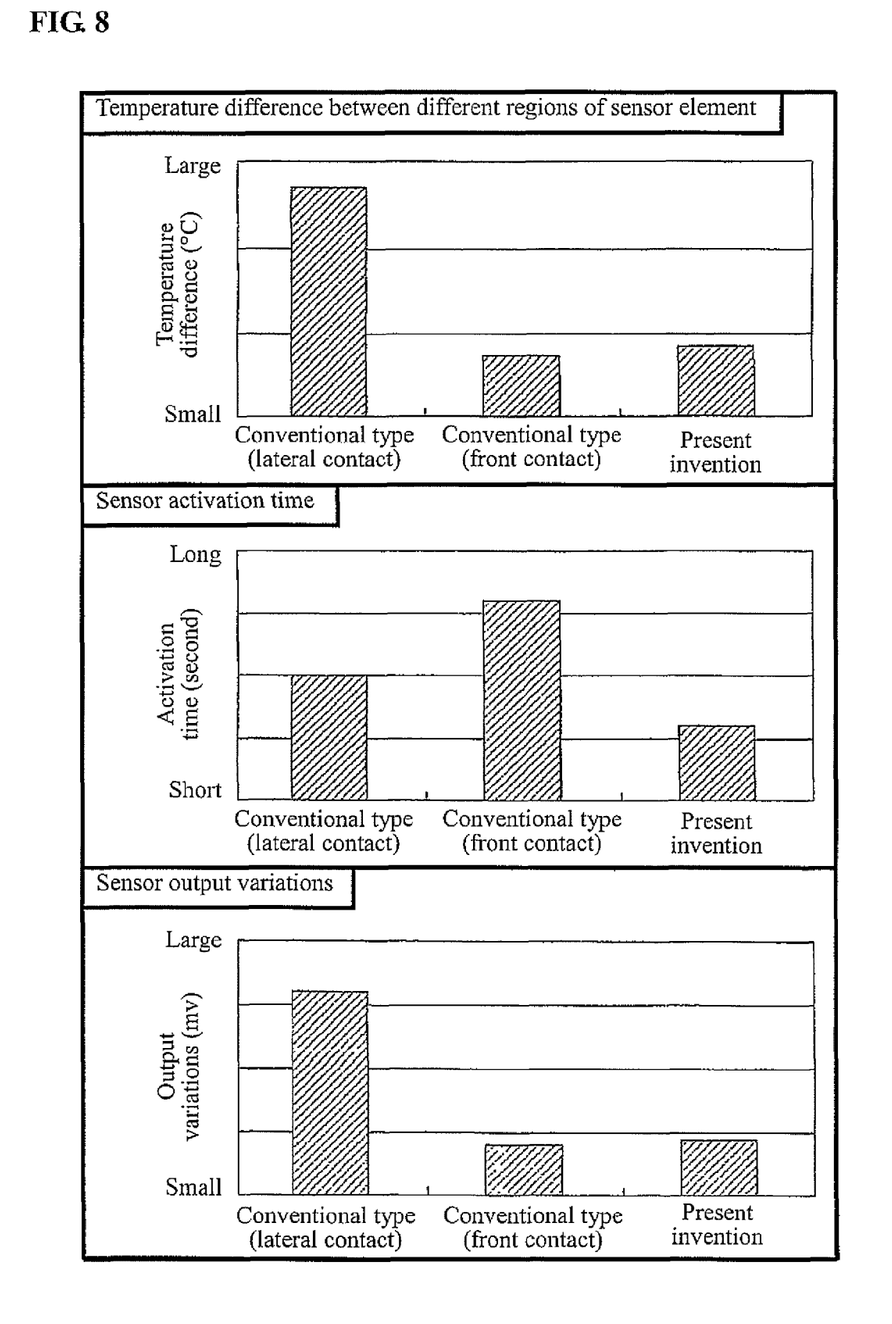
FIG. 8 is graphs showing measurement results of a gas sensor to which the present invention is applied and two comparative (conventional) gas sensors.

FIG. 8 is graphs showing the results of the measurement test about "temperature difference between different sensor element regions", "sensor activation time" and "sensor output variations". Herein, the "temperature difference between different sensor element regions" refers to a difference in temperature between a maximum heat generation region of the outer circumferential surface of the sensor element and a region located opposite the maximum heat generation region in the circumferential direction of the sensor element (i.e. shifted 180 degrees in the circumferential direction).

As is seen from the measurement test results of FIG. 8, the "temperature difference between different sensor element regions" of the lateral-contact-structure gas sensor was the largest. The "temperature difference between different sensor element regions" of the gas sensor according to the present invention and the "temperature difference between different sensor element regions" of the front-contact-structure gas sensor were smaller than that of the lateral-contact-structure gas sensor. It is apparent from these measurement test results that, as compared to the lateral-contact-structure gas sensor, the gas sensor according to the present invention was able to effectively prevent the nonuniform temperature distribution of the sensor element.

The "sensor activation time" of the front-contact-structure gas sensor was the longest. The "sensor activation time" of the lateral-contact-structure gas sensor was shorter than that of the front-contact-structure gas sensor. The "sensor activation time" of the gas sensor according to the present invention was further shorter than that of the lateral-contact-structure gas sensor. It apparent from these measurement test results that the gas sensor according to the present invention was able to effectively reduce the sensor activation time as compared to the front-contact-structure gas sensor and the lateral-contact-structure gas sensor.

The "sensor output variations" of the lateral-contact-structure gas sensor was the largest. The "sensor output variations" of the gas sensor according to the present invention and the "sensor output variations" of the front-contact-structure gas sensor were smaller than those of the lateral-contact-structure gas sensor. It is apparent from these measurement test results that, as compared to the lateral-contact-structure gas sensor, the gas sensor according to the present invention was unlikely to cause output variations.

To sum up, it has been shown by the above measurement test results that it is possible for the gas sensor according to the present invention to effectively reduce the time required for activation of the element body of the gas sensing element (sensor element) and limit variations in the output from the element body of the gas sensing element (sensor element) as compared to the front-contact-structure gas sensor and the lateral-contact-structure gas sensor.

The invention claimed is:

1. A gas sensor, comprising:
   a sensor element made of a solid electrolyte and having a cylindrical portion arranged coaxially with an axis of the sensor element, a front end portion closing a front end of the cylindrical portion, and a connection region connecting the cylindrical portion and the front end portion; and
   a heater formed into either a cylindrical shape or a columnar shape and located inside the sensor element so as to heat the sensor element by heat generation thereof;
   wherein the heater has a front end portion and a lateral portion which meets the front end portion at an interface between the front end portion and the lateral portion;
   wherein the front end portion of the heater is in contact with an inner surface of the front end portion of the sensor element;
   wherein the lateral portion of the heater that is to the rear of the interface is in contact with an inner circumferential surface of the cylindrical portion of the sensor element; and
   wherein a chamfered portion is formed on a front end edge of the heater and kept from contact with the inner surface of the front end portion and the connection region of the sensor element.

2. The gas sensor according to claim 1, wherein the inner surface of the front end portion of the sensor element is made flat.

3. The gas sensor according to claim 1, wherein the connection region is defined as an arc curved surface along a boundary between the inner surface of the front end portion and the inner circumferential surface of the cylindrical portion such that the inner surface of the front end portion and the inner circumferential surface of the cylindrical portion are connected smoothly by the connection region.

4. The gas sensor according to claim 1, wherein the sensor element satisfies a relationship of 0.3≤r/R where R is a diameter of the inner circumferential surface of the cylindrical portion; and r is a diameter of the inner surface of the front end portion.

5. The gas sensor according to claim 4, wherein the sensor element satisfies a relationship of r/R=0.47 where R is the diameter of the inner circumferential surface of the cylindrical portion; and r is the diameter of the inner surface of the front end portion.

6. The gas sensor according to claim 1, wherein the front end portion of the sensor element has an outer surface defining a front end of the sensor element; and wherein both of the inner and outer surfaces of the front end portion of the sensor element are made flat.

7. The gas sensor according to claim 6, wherein a thickness of the front end portion of the sensor element in a direction of the axis is larger than or equal to a radial thickness of a region of the cylindrical portion of the sensor element with which the heater is brought into contact.

8. The gas sensor according to claim 1, wherein a thickness of the front end portion of the sensor element in a direction of the axis is equal to a radial thickness of a region of the cylindrical portion of the sensor element with which the heater is brought into contact.

9. The gas sensor according to claim 1,
   wherein the heater includes a ceramic rod, a ceramic layer covering an outer circumference of the ceramic rod, with a front end portion of the ceramic rod protruding from a front end of the ceramic layer, and a heating element disposed in a front end part of the ceramic layer;
   wherein the front end portion of the ceramic rod is in contact with the inner surface of the front end portion of the sensor element; and
   wherein the heating element or ceramic layer is in contact with the inner circumferential surface of the cylindrical portion of the sensor element.

10. The gas sensor according to claim 1, wherein a chamfered portion is formed on a front end edge of the front end portion of the heater, the chamfered portion extending between the lateral portion and the front end portion of the heater, which chamfered portion is not in contact with the inner surface of the front end portion of the sensor element and is not in contact with the connecting region of the sensor element.

* * * * *